US005223393A

United States Patent [19]
Khanna et al.

[11] Patent Number: 5,223,393
[45] Date of Patent: Jun. 29, 1993

[54] DETECTION OF ANALYTES HAVING BINDING SITES FOR AT LEAST TWO BINDING MOIETIES

[75] Inventors: Pyare Khanna, Fremont; Reuyming Loor, Danville, both of Calif.

[73] Assignee: Microgenics Corporation, Concord, Calif.

[21] Appl. No.: 537,905

[22] Filed: Jun. 12, 1990

[51] Int. Cl.$^5$ .................. C12Q 1/68; C12Q 1/00; G01N 33/53; G01N 33/566
[52] U.S. Cl. ........................ 435/6; 435/7.6; 435/7.8; 436/501; 436/514; 436/517; 436/532; 436/533; 436/534
[58] Field of Search ............ 435/7.6, 7.8, 5.6, 6; 436/501, 514, 517, 532, 533, 534

[56] References Cited

U.S. PATENT DOCUMENTS

| | | | |
|---|---|---|---|
| 4,378,428 | 3/1983 | Farina et al. | 435/7 |
| 4,514,505 | 4/1985 | Canfield et al. | 436/500 |
| 4,663,278 | 5/1987 | DiNello | 435/7 |
| 4,708,929 | 11/1987 | Henderson | 435/7 |
| 4,868,130 | 9/1989 | Hargreaves | 436/526 |
| 4,943,525 | 7/1990 | Dawson | 435/7 |
| 4,956,274 | 9/1990 | Khanna et al. | 435/7 |
| 5,032,503 | 7/1991 | Khanna et al. | 435/7.6 |
| 5,037,735 | 8/1991 | Khanna et al. | 435/7.6 |

FOREIGN PATENT DOCUMENTS

| | | |
|---|---|---|
| 0144914A2 | 6/1985 | European Pat. Off. |
| 0315364A3 | 5/1989 | European Pat. Off. |
| 0419081A2 | 3/1991 | European Pat. Off. |
| WO89/02597 | 3/1989 | World Int. Prop. O. |

OTHER PUBLICATIONS

Henderson et al (1986) CEDIA TM A New Homogeneous Immunoassay, Clin Chem 32:1637–1641.

*Primary Examiner*—Christine M. Nucker
*Assistant Examiner*—D. R. Preston
*Attorney, Agent, or Firm*—Cooley Godward Castro Huddleson & Tatum

[57] ABSTRACT

The present invention provides reagents for a detectable label for use in specific binding assays. Specifically, modified $\beta$-galactosidase enzyme donors (ED) and acceptors (EA) are utilized. Both ED and EA are modified to form separate ED and EA complexes by coupling each with a linking element and a binding moiety which is specific to a binding site in the analyte. The ED and EA complexes are incapable of forming active enzyme in the absence of the analyte. However, when analyte is present, ED and EA complexes which bind to a common analyte in a sample, active $\beta$-galactosidase is formed.

19 Claims, No Drawings

5,223,393

DETECTION OF ANALYTES HAVING BINDING SITES FOR AT LEAST TWO BINDING MOIETIES

TECHNICAL FIELD

The present invention relates to enzyme immunoassays and, in particular, to immunoassays using β-galactosidase as the enzyme label.

BACKGROUND

Enzyme immunoassays have been a very successful type of homogeneous immunoassay. A number of such assays have been based on the ability of fragments of β-galactosidase to complement each other and form active enzyme. In particular, a β-galactosidase enzyme donor (ED) combines with a β-galactosidase enzyme receptor (EA) to form active β-galactosidase enzyme. Conjugating a small analyte or an analyte analogue to the ED at certain sites does not affect the complementation of ED to EA or the rate of β-galactosidase catalyzed activity. However, when the ED-analyte conjugate is bound by anti-analyte antibody, complementation and the enzyme-catalyzed reaction rate during the initial phase of the reaction is reduced. This reduction in enzyme-catalyzed reaction rate has been used to quantify analytes in a situation where both the ED-analyte conjugate present in an assay medium and the analyte present in the sample compete for anti-analyte antibody prior to the addition of EA. The β-galactosidase catalyzed reaction rate increases as the amount of analyte present in the sample increases, because more analyte in the sample reduces interaction of the ED-analyte conjugate and anti-analyte antibody, allowing more of the ED-analyte conjugate to react with the EA to form active β-galactosidase enzyme.

This technology has generally been limited to low molecular weight analytes. The present invention provides a method capable of measuring high molecular weight analytes.

Relevant Literature

Modified β-galactosidase enzyme donors and enzyme acceptors have been prepared by chemical synthesis and recombinant DNA engineering. The modified fragments retain β-galactosidase activity upon complementation. See, for example, U.S. Pat. Nos. 4,708,929 and 3,378,428 and the articles cited therein. Mutant polypeptides derived from β-galactosidase are disclosed by Langley and Zabin, *Bio. Chem.* (1976) 15:4866, which can complement or spontaneously restore enzyme activity when added to extracts of appropriate β-galactosidase negative mutants. See also Lin et at., *Bio. Chem. Biophys. Res. Comm.* (1970) 40:249.

SUMMARY OF THE INVENTIONS

It is an object of this invention to provide a method and reagents for the detection and quantitative analysis of analytes, particularly high molecular weight analytes, having binding sites for at least two binding moieties.

The present invention provides such a method and reagents by utilizing modified β-galactosidase enzyme donors and enzyme acceptors. Specifically, the presence or quantity of an analyte having binding sites for at least two binding moieties in a sample is determined by employing complementary fragments of β-galactosidase, which fragments are defined as enzyme donor (ED) and enzyme acceptor (EA) and when bound, i.e., brought together, form active β-galactosidase, wherein the ED and EA are modified to form separate ED and EA complexes by coupling each with a linking element and a binding moiety which is specific to a binding site on the analyte. The ED and EA complexes are incapable of forming active enzyme in the absence of the analyte. When analyte is present, however, ED and EA complexes which bind to a common analyte in a sample are brought together so that they form active β-galactosidase enzyme.

The resulting enzyme activity can be detected or measured in a variety of well-known manners, such as by using an enzyme substrate which provides a measurable product upon reaction with β-galactosidase. The amount of analyte present in the sample can thereby be determined by comparing the amount of measurable product to that formed from a known amount of analyte.

DESCRIPTION OF SPECIFIC EMBODIMENTS

The present invention comprises methods and reagents for detecting and quantitating the amount of an analyte in a sample. In particular, the present invention provides a method for detecting the presence of an analyte having binding sites for at least two binding moieties in a sample employing complementary fragments of β-galactosidase, which fragments are defined as enzyme donor (ED) and enzyme acceptor (EA) and when bound from active β-galactosidase, which method comprises:

(a) providing an ED complex comprising ED coupled via a linking element to a first binding moiety and an EA complex comprising EA coupled via a linking element to a second binding moiety, wherein the first and second binding moieties are specific for binding sites on the analyte and the ED complex and EA complex are incapable of forming active enzyme in the absence of the analyte, (b) contacting the ED complex and EA complex with the sample, and (c) relating the presence of the analyte in the sample to the formation of active enzyme.

The present inventive method further contemplates the ED complex, EA complex, and sample being contacted with an enzyme substrate which provides for a measurable product upon reaction with β-galactosidase such that the amount of analyte in the sample can be determined by comparing the amount of measurable product to that formed in the presence of a known amount of analyte. The present invention also contemplates kits for use in carrying out the method of the present invention.

The present invention is predicated, at least in part, on the principle that the ED/linking element/binding moiety complex and EA/linking element/binding moiety complex only form active enzyme when each has bound to a common analyte through their respective binding moieties. The quantity of analyte, therefore, is directly proportional to enzyme activity, which can be measured in any suitable manner, as through the use of an enzyme substrate. The inability of the ED complex to complement the EA complex in the absence of analyte differs markedly from the β-galactosidase complementation phenomenon observed in a number of previously described assays employing ED and EA conjugates. For example, in the assays described in U.S. Pat. No. 4,708,929, ED conjugated to analyte complements EA unless anti-analyte antibodies are added to the assay mixture. This difference is believed to result from the large size of the binding moieties and/or linking moieties relative to the size of the analytes that were attached to the ED and EA moieties in the assays that operated by this different principle.

The ED and EA components are partial sequences of $\beta$-galactosidase. For purposes of the subject invention, the N-terminal portion of the $\beta$-galactosidase is referred to as the enzyme donor (ED), and the C-proximal portion is the enzyme acceptor (EA). The enzyme acceptor and enzyme donor are characterized by forming an active enzyme complex when brought together. The preparation of $\beta$-galactosidase enzyme donors and acceptors is described in U.S. Pat. No. 4,708,929, which disclosure is incorporated herein by reference.

The linking elements of the ED and EA complexes can be the same or different and can comprise any material which, in combination with the binding moiety, prevents the EA and ED complexes from forming an active enzyme in the absence of binding to a common analyte. The linking elements preferably will comprise particles of beads having an average diameter of about $0.01\mu$ to about $0.1\mu$, most preferable about $0.05\mu$ to about $0.08\mu$. Suitable linking materials for the linking elements include organic polymers, both naturally occurring and synthetic, such as polysaccharides, styrene polymers, polyacrylates, e.g., polyacrylamide, hydroxyethyl polymethacrylates, glass, ceramic, carbon, polyvinyl chloride, protein, and the like. Styrene polymers include polystyrene, polymers containing aromatic moieties, and higher aromatic compounds such as napthalene, anthracene, etc. The linking elements of the ED and EA complexes preferably are the same and consist of a latex compound.

Alternatively, bifunctional organic linking groups can be used to attach the EA or ED component to the binding moiety. Examples of such groups, which are well known in protein chemistry, include dialdehydes, such as glutaraldehyde, and diamines, such as 1,6-diaminohexane. Such bifunctional organic linking groups are preferably used when the binding moiety is sufficiently large to prevent complementation without requiring the presence of a large linking element.

The various linking elements can be functionalized or non-functionalized, preferably functionalized for covalent bonding to the binding moiety. When the linking element is a polymeric material, various procedures are known in the art for the activation of polymer surfaces and the attachment of immunoglobulins, glycoproteins, saccharide-containing organic molecules, and polynucleotides. See U.S. Pat. Nos. 4,419,444; 4,775,619; 3,956,219; and 3,860,486 as well as European Patent Application No. 84308143.1 and Scouten, W. H. (ed.) *Solid Phase Biochemistry, Analytical and Synthetic Aspects* (1983), Wiley & Sons, New York, page 779.

The binding moieties are components capable of binding to the particular analyte of interest. The binding between the binding moieties and the analyte is preferably non-covalent. Suitable binding moieties preferably have higher affinity and specificity for the analyte than for the other components in a sample for analysis. Suitable binding moieties can be of a variety of molecular categories including antibodies, in particular, and preferably, monoclonal antibodies specific for a portion of the analyte; binding proteins that naturally bind to the analyte, e.g. lectins for analytes comprising a carbohydrate portion; and ligand receptors when the analyte comprises a complementary ligand.

The binding moiety of the ED complex and the binding moiety of the EA complex can be of the same or different categories; e.g., both binding moieties can be antibodies or the binding moiety component of the EA complex can be an antibody and the binding moiety component of the ED complex can be a lectin.

When the analyte is a nucleic acid, the binding moiety can be ssDNA, RNA, or any other natural or synthesized single stranded nucleic acid. Alternatively the binding moiety could be a non-nucleic acid molecule which recognizes a specific nucleotide sequence, such as an antibody or specific DNA binding protein on the analyte.

Methods for the production of antibodies or monoclonal antibodies to be used in the subject invention are known in the literature. See, e.g., U.S. Pat. No. 4,574,116 and the references cited therein, whose disclosures are herein incorporated by reference. Alternatively, monoclonal antibodies or binding fragments can be purchased commercially.

When the binding moiety is a nucleic acid molecule, the moiety will usually comprise at least 8 nucleotides, more usually 10 nucleotides, and preferably at least about 12 nucleotides. The size of the binding moiety will vary with the nature of the analyte, the amount of analyte in the sample, and the conditions employed in the detection process. The nucleic acid sequences for use in a binding moiety can be provided by isolation from a natural source, synthesis, or other means known in the art.

The present invention provides for assays of higher specificity than the specificity arising from a single binding interaction between the binding moiety of either the ED or EA complex and the target analyte. Thus binding moieties of relatively low specificity for the analyte can be used in ED and EA completed to provide for a highly specific assay. The high specificity of the present invention is obtained because the production of $\beta$-galactosidase activity is contingent upon the occurrence of two independent binding events. A specific binding interaction must occur between the analyte and both of the binding moieties in order for ED and EA to complement one another.

The assay method of the invention can be used to detect any analyte that is capable of binding simultaneously to the binding moieties of the ED and EA complexes. Generally, the analyte will be a polypeptide, protein, polysaccharide, nucleic acid, or combination thereof.

For the most part, the analytes detected or quantified in accordance with the present invention will preferably have a molecular weight of at least about 5,000, more usually at least about 10,000. Polypeptides of interest will generally be from about 5,000 to about 5,000,000 molecular weight, more usually from about 10,000 to 1,000,000 molecular weight. Where the analyte is a nucleic acid molecule, the molecule will generally range from about 12 nucleotides to about $2 \times 10^6$ nucleotides. The nucleic acid sample can involve DNA, which can be chromosomal or extrachromosomal, e.g., plasmids, viruses, synthetic constructs, or the like, or RNA, such as messenger RNA, transfer RNA, ribosomal RNA, viruses, or the like. The nucleic acid sequences can involve structural genes on translated regions, regulatory regions, introns, exons, and the like. Analytes for detection or quantitative with the present invention can also have molecular weight of less than about 5,000. Examples of suitable analytes with a molecular weight of less than 5,000 include small polynucleotides, small polypeptide hormones, steroid hormones, cholesterol, drugs, and toxins. However, such small analytes must be capable of binding two separate binding moieties as described herein.

The protocol for the assay can be varied widely, depending upon the system being employed, the sensitivity of the assay, the speed with which the assay is to be carried out, the nature of the analyte, and the like. The EA and ED complexes and sample are combined together under appropriate conditions of stringency to allow for binding. The reagents can be combined concomitantly or added sequentially. Where the order is sequential, the reaction mixture of sample, ED complex, EA complex, and buffer is preferably incubated for about 5 to 25 minutes, usually about 15 minutes, before the addition of enzyme substrate.

The sample can be subjected to prior preparation or can be used without prior treatment. In the situation in which the analyte in the sample is capable of binding with the binding moieties, no prior sample preparation is generally necessary. In the situation in which the analyte in the sample is not immediately capable of binding with the binding moieties, prior sample preparation will be necessary. For example, where the analyte is doubled stranded nucleic acid and the binding moieties are complementary nucleic acid strands, it will be necessary to treat the sample to denature the double-stranded molecules before mixing with the ED and EA complexes. Denaturation can be achieved most readily by subjecting the sample to high temperature, generally from about 90° C. to about 100° C. for about 3 to about 15 minutes. Other means for denaturation can be utilized such as treating the sample with alkaline solutions or concentrated solutions of formamide or through use of other procedures known in the art.

The assay medium is preferably buffered at a pH in the range of about 6 to 9, with a convenient buffer such as phosphate, tris, or the like. The significant factor in selecting an appropriate buffer is that the buffer not inhibit the enzyme reaction or binding.

The assay can be carried out at any suitable temperature which does not inhibit the desired reactions, generally about 20° C., but preferably at an elevated temperature below about 40° C. The assays are generally and preferably performed at atmospheric pressure.

The times required for the completion of the desired reactions vary depending on the particulars of the assays. In the situations, for example, in which the binding moiety is a nucleic acid, the time required for hybridization or binding depends on the concentration and sequence complexity of the nucleic acid probe, as well as on the assay temperature, solvent, and salt concentrations. Generally, hybridization is carried out at a temperature of about 20° C. to about 50° C. in about 0.15M sodium chloride and 0.015M sodium citrate for a period of about ½ hr. to about 18 hr. to allow formation of hybrids.

The techniques for the hybridization of DNA are disclosed in many references, including Walker and Gaastra (eds.) *Techniques in Molecular Biology* (1983) MacMillan Publishing Company, New York, pp 113-135 and 273-283; Maniatis et al., (eds) *Molecular Cloning* (1982) Cold Spring Harbor Laboratory, pp 309; E. Southern, *J. Mol. Biol.* (1875) 98:503; Botchan et al., *Cell* (1976) 9:269; Jeffreys et al., *Cell* (1977) 12:429. These disclosures are incorporated herein by reference.

The amount of sample that can be used in conjunction with the present invention depends, among other things, upon the concentration of the analyte, the nature of the sample, and the sensitivity of the assay.

In using the present invention, any suitable means can be used to detect and quantify the amount of active enzyme and relate the information to the detection and determination of the amount of analyte present in the sample. An enzyme substrate is generally and preferably used for such a purpose by providing a measurable product upon reaction with active $\beta$-galactosidase enzyme. The amount of analyte in the sample can then be determined by comparing the amount of measurable product to that formed in the presence of a known amount of analyte.

The enzyme substrate typically and preferably employed results in a change in the amount of light absorbance (optical density) or emission of the assay medium when cleaved by the active enzyme. That is, cleavage of the substrate results in the appearance or disappearance of a colored or fluorescent product. Preferred enzyme substrates include o-nitrophenyl galactoside (ONPG) and chlorophenol red-$\beta$-galactosidase (CPRG). ONPG, CPRG, and other comparable enzyme substrates are commercially available. ONPG is generally used in a concentration of from about 0.5 to about 2.0 mg/ml. Other substrates are used in concentrations to provide comparable signals to ONPG.

Where the ED and EA complexes are combined in an appropriate assay medium with the enzyme substrate with the subsequent addition of the sample, a first reading can be taken to provide a background measurement of enzyme activity. For the most part, a mixture of the ED and EA complexes yields zero reaction, although a low level of enzyme activity resulting from complementation is acceptable. The essential requirement of this background activity is that it be distinguishable from activity in the presence of the detectable limit of analyte.

After addition of the sample, one or more additional readings can be taken after incubation, the interval varying from about 1 minute to about 1 hour, usually about 5 minutes to about 15 minutes, between the readings. While a single reading can be taken, it is usually desirable to take more than one reading so that common errors can be cancelled out. Preferably, standard solutions are prepared of known concentrations of analyte to serve as standards for comparison with the sample. In this way, accurate quantitative determinations can be obtained.

The present invention also contemplates a kit containing reagents for carrying out the present inventive method. The kit comprises in at least one container, usually in separate containers, a $\beta$-galactosidase enzyme donor complex and enzyme acceptor complex. The container(s) of enzyme donor complex and enzyme acceptor complex can additionally contain enzyme substrate or enzyme substrate can be provided separately. Alternatively, the kits can be configured so that they contain ED and EA separately attached to linking elements, without their respective binding moieties. Upon attachment of particular binding moieties to the ED and EA linking elements of the kit, the desired analyte of interest can be assayed.

The following example is offered by way of illustration and not by way of limitation of the present invention.

EXAMPLE

Assay Principle

Two latex preparations were used in this assay format for the measurement of hCG (human chorionic gonadotropin). One latex preparation was latex coupled with ED (enzyme donor) and MAb (monoclonal antibody) to α-subunit of hCG, and the other latex preparation was latex coupled with EA (enzyme acceptor) and MAb to β-subunit of hCG. The mixture of latex preparations gives zero reaction or assay background when there is no antigen (hCG) present in the assay. With various concentrations of antigen in the assay, ED and EA were brought together to form active enzyme by antigen-antibody binding, thereby exhibiting enzyme activity proportional to antigen concentration. An assay calibration curve was constructed from the assay absorbance at various concentrations of antigen, and the unknown hCG was measured by reference to the calibration curve.

Materials

Carboxyl-modified latex (70 nm diameter) in a 15% solid solution was purchased from Polymer Laboratories, Ltd., Essez Road, Church Stretton, U.K. Human Chorionic Gonadotropin (hCG) was obtained from Sigma Chemical Company. EDAC (1-ethyl-3-[3-dimethyl amimopropyl]carbodiimide) and sulfo-NHS (N-hydroxy sulfosuccinimide) were bought from Pierce Chemical Company. Monoclonal antibody to α and β-subunit of hCG were purchased from Medix Biochemica, Helsincei, Finland. CPRG (chlorophenol red β-galactosidase) was obtained from Boehringer Mannhheim. Enzyme donor and acceptor were prepared as set forth in U.S. Pat. No. 4,708,929, whose disclosure is herein incorporated by reference. Other chemicals were purchased from Sigma Chemical Company.

Latex Conjugate Preparation

1. Activation of Latex

One ml of latex solution was washed with 50 ml of 0.1M sodium carbonate, pH 9.6, using an Amicon concentrator device. The washing step was repeated once. The latex was then washed twice each with 50 ml of 0.02M sodium phosphate, pH 4.5. The latex was resuspended in 2 ml of 0.02M sodium phosphate, pH 4.5, and added to an equal volume of 2% EDAC in the same buffer. The mixture was incubated in an end-to-end mixer for 3 hours at room temperature. An equal volume of 3% sulfo-NHS can be added to enhance coupling efficiency. After incubation, the activated latex was washed twice each with 50 ml of 0.2M borate buffer, pH 8.5, and then resuspended in 4 ml of the same buffer.

2. Latex Coupling with ED and MAb to α-subunit of hCG

A mixture of 1.2 ml of 1 mg ED4 and 1 mg MAb to a α-subunit was added to 2 ml of activated latex. The mixture was incubated overnight at 4° C. on an end-to-end mixer. After incubation, the latex was washed twice each with 50 ml of 0.2M borate buffer, pH 8.5, and then resuspended in 2 ml of the same buffer. To the latex suspension, 50 μl of 0.25 ethanolamine was added per ml of solution, and the mixture was then incubated for 30 minutes at room temperature. The latex solution was washed twice with 50 ml of 0.2M borate buffer, pH 8.5, and resuspended in 5 ml of the same buffer. An equal volume of borate buffer containing 2% bovine serum albumin (BSA), 2% L-aspartyl-L-phenylalanine methyl ester, and 0.2% PVP (polyvinyl pyrrolidone) was added to the latex suspension, and the mixture was incubated overnight at 4° C. The latex was washed twice with with 50 ml borate buffer and resuspended in 5 ml of storage buffer (0.1M sodium phosphate, pH 7.4, 0.15M NaCl, 1% BSA, 5% glycerol, and 0.1% sodium azide) at 4° C. until used.

3. Latex Coupling with EA and MAb to β-subunit of hCG

One ml of 5 mg ovomucoid in 0.2M borate buffer, pH 8.5, was added to 2 ml of activated latex, and the mixture incubated overnight at 4° C.. After incubation, 50 μl of 0.25M ethanolamine was added per ml of latex suspension. The mixture was incubated for 30 minutes at room temperature and then washed twice each with 50 ml of phosphate buffered saline (20 mM sodium phosphate, pH 7.5, and 0.15M NaCl) using an Amicon concentrator device. The latex was washed with 50 ml of 0.1M sodium acetate buffer, pH 4.5, and a final volume of 5 ml was kept. An equal volume of 0.2M sodium periodate in 0.1M sodium acetate, pH 4.5, was added to the latex suspension. The mixture was incubated for 20 minutes in the dark at room temperature. After incubation, the latex was washed with 30 ml of 0.1M sodium acetate, pH 4.5, and 30 ml of 0.1M sodium acetate, pH 6.5. The latex was then resuspended in 5 ml of 0.1M sodium acetate, pH 6.5. One ml of solution containing 1 mg EA and 1 mg MAb to β-subunit of hCG was added to the latex suspension. Solid sodium cyano-borohydride was immediately added to a final concentration of 1 mg/ml, and the mixture incubated overnight at 4° C.. The latex suspension was washed twice with 50 ml of 0.2M borate buffer, pH 8.5, and resuspended in 5 ml of the same buffer. An equal volume of borate buffer containing 2% BSA, L-aspartyl-L-phenylalanine methyl ester, and 0.2% PVP was added to the latex suspension, and the mixture was incubated overnight at 4° C. The latex was washed with 30 ml borate buffer and resuspended in storage buffer (0.1M sodium phosphate, pH 7.4, and 0.15M NaCl, 1% BSA, 5% glycerol, and 0.1% sodium azide) at 4° C. until used.

Assay Procedures

Two procedures were used for the measurement of hCG. Prior to assay, both latex preparations were separately washed with 50 ml EA buffer and resuspended to an appropriate volume. EA buffer consists of 60 mM MOPS buffer, pH 6.85, 200 mM NaCl, 10 mM EGTA, 3% ethylene glycol, 0.05% Tween 20, 0.05 mM DTT, 3 mM magnesium acetate and 0.1% sodium azide.

1. Procedure One

Procedure one involved a simultaneous addition of all reagents. To each tube, 20 μl calibrators (0, 500, 1000, and 2000 mIU/ml hCG) in human serum base, 120 μl EA buffer, 20 μl of EA/MAb/latex (1 μl equivalent latex), 20 μl ED/MAb/latex (1 μl equivalent latex), and 20 μl CPRG (1 mg/ml in EA buffer) were added, and the mixtures incubated for 15 minutes at 37° C. After incubation, the reaction mixtures were centrifuged for 10 minutes in a microfuge at 4° C. The supernatants were removed. The pellets remaining were each resuspended in 100 μl EA buffer and transferred to microtiter plate wells. After mixing, the absorbance of each well was read at 570 nm wavelength using a microtiter plate reader.

2. Procedure Two

Procedure two involved a sequential addition of substrate. To each tube, 20 μl calibrators (0, 1000, and 5000 mIU/ml hCG) in human serum base, 10 μl EA/MAb/-latex (1 μl equivalent latex), 10 μl ED/MAb/latex (1 μl equivalent latex), and 100 μl EA buffer were added and incubated for 15 minutes at 37°C. The reaction mixtures were then centrifuged for 6 minutes at 4° C. in a microfuge. The supernatants were removed. The pellets remaining were each resuspended with 150 μl CPRG (1 mg/ml) in EA buffer and transferred to microtiter plate wells. After incubation for 60 minutes at room temperature, the absorbance of each tube was read at 570 nm wavelength using a microtiter plate reader.

Results

Using procedure one (simultaneous addition of substrate), the following results were obtained.

TABLE 1

|   | hCG (mIU/ml) | A(570 nm) |
|---|---|---|
| 1 | 0.000 | 0.958 |
| 2 | 500.000 | 1.056 |
| 3 | 1000.000 | 1.337 |
| 4 | 2000.000 | 1.491 |

A calibration curve for HCG assay can be constructed from the results. The color development due to active enzyme formation from two latex conjugates brought together by antigen-antibody interaction was proportional to the concentration of HCG in the assay system.

When procedure two (sequential addition of substrate) was followed, the following results were obtained.

TABLE 2

|   | hCG (mIU/ml) | A(570 nm) |
|---|---|---|
| 1 | 0.000 | 0.744 |
| 2 | 1000.000 | 0.833 |
| 3 | 5000.000 | 0.971 |

It is evident from the above results that the subject method provides for an accurate, sensitive, and rapid technique for detecting levels of analytes, particularly in a complex mixture. The observed enzyme activity is proportional to the amount of analyte in the sample. The method is particularly suited to the measurement of high molecular weight analytes which are not readily amenable to measurement by known assay techniques.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

What is claimed is:

1. A method for detecting the presence of an analyte having binding sites for at least two binding moieties in a sample employing complementary fragments of β-galactosidase, which fragments are defined as enzyme donor (ED) and enzyme acceptor (EA) which when bound together form active β-galactosidase, which method comprises:

(a) providing an ED complex comprising ED coupled via a first linking group to a first binding moiety on said analyte and an EA complex comprising EA coupled via a second linking group to a second binding moiety on said analyte, wherein the first and second binding moieties are specific for said at least two binding sites for said analyte whereby the ED complex and EA complex are hindered from forming said active enzyme in the absence of said analyte, (b) contacting the ED complex and the EA complex with said sample and an enzyme substrate, and (c) relating the presence of said analyte in said sample to the formation of said active enzyme by detecting a measurable product of the action of said active enzyme on said substrate.

2. A method according to claim 1, wherein said analyte is a polypeptide.

3. A method according to claim 1, wherein said analyte has a molecular weight of at least 5,000.

4. A method according to claim 1, wherein said analyte has a molecular weight of at least 10,000.

5. A method according to claim 1, wherein said analyte is a nucleic acid.

6. A method according to claim 5, wherein said nucleic acid is DNA.

7. A method according to claim 5, wherein said nucleic acid is RNA.

8. A method according to claim 1, wherein said binding moieties are antibodies.

9. A method according to claim 8, wherein said antibodies are monoclonal antibodies.

10. A method according to claim 1, wherein said binding moieties are nucleic acid.

11. A method according to claim 1, wherein said substrate is chlorophenol red-β-galactosidase (CPR).

12. A method according to claim 1, wherein said first and second linking groups are latex beads.

13. A kit for use in detecting the presence of an analyte having binding sites for at least two binding moieties in a sample employing complementary fragments of β-galactosidase, which fragments are defined as enzyme donor (ED) and enzyme acceptor (EA) and when bound form active β-galactosidase, which kit comprises:

an ED complex comprising ED coupled via a linking group to a first binding moiety on said analyte, and an EA complex comprising EA coupled via a linking group to a second binding moiety on said analyte, wherein the first and second binding moieties are specific to said at least two binding sites on said analyte whereby the ED complex and the EA complex are hindered from forming said active enzyme in the absence of said analyte.

14. The kit according to claim 13, which kit further comprises an enzyme substrate which provides a measurable product upon reaction with β-galactosidase and allows for the determination of the amount of said analyte in the sample by comparison with the amount of measurable product formed from a known amount of analyte.

15. A kit according to claim 14, wherein said binding moieties are antibodies.

16. A kit according to claim 15, wherein said antibodies are monoclonal antibodies.

17. A kit according to claim 14, wherein said binding moieties are nucleic acids.

18. A kit according to claim 14, wherein said substrate is chlorophenol red-$\beta$-galactosidase (CPR).

19. A kit according to claim 14, wherein said first and second linking groups are latex beads.

* * * * *